(12) United States Patent
Faulkner et al.

(10) Patent No.: US 12,109,195 B2
(45) Date of Patent: Oct. 8, 2024

(54) COMPOSITIONS AND METHODS FOR TREATMENT OF VAGINAL INFECTIONS

(71) Applicant: Vireo Systems, Inc., Madison, TN (US)

(72) Inventors: Mark C. Faulkner, Madison, TN (US); Deeannah Seymour, Franklin, TN (US)

(73) Assignee: Vireo Systems, Inc., Madison, TN (US)

( * ) Notice: Subject to any disclaimer, the term of this patent is extended or adjusted under 35 U.S.C. 154(b) by 176 days.

(21) Appl. No.: 17/363,193

(22) Filed: Jun. 30, 2021

(65) Prior Publication Data

US 2021/0401806 A1   Dec. 30, 2021

Related U.S. Application Data

(60) Provisional application No. 63/045,897, filed on Jun. 30, 2020.

(51) Int. Cl.

| | | |
|---|---|---|
| *A61K 31/41* | (2006.01) | |
| *A61K 9/00* | (2006.01) | |
| *A61K 9/02* | (2006.01) | |
| *A61K 31/194* | (2006.01) | |
| *A61K 31/4168* | (2006.01) | |
| *A61K 31/7016* | (2006.01) | |
| *A61K 31/702* | (2006.01) | |
| *A61K 31/733* | (2006.01) | |
| *A61K 33/22* | (2006.01) | |
| *A61K 35/747* | (2015.01) | |
| *A61P 31/04* | (2006.01) | |

(52) U.S. Cl.
CPC ........ *A61K 31/4168* (2013.01); *A61K 9/0036* (2013.01); *A61K 9/02* (2013.01); *A61K 31/194* (2013.01); *A61K 31/7016* (2013.01); *A61K 31/702* (2013.01); *A61K 31/733* (2013.01); *A61K 33/22* (2013.01); *A61K 35/747* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 4,981,686 A | 1/1991 | Hardy | |
| 5,122,407 A | 6/1992 | Yeo et al. | |
| 5,176,911 A * | 1/1993 | Tosi | A61P 13/02 |
| | | | 435/252.9 |
| 5,714,165 A | 2/1998 | Repka et al. | |
| 6,017,521 A | 1/2000 | Robinson et al. | |
| 6,420,425 B1 | 7/2002 | Melman | |
| 7,276,056 B2 | 10/2007 | Abbott et al. | |
| 8,349,368 B2 | 1/2013 | Gordon et al. | |
| 8,586,549 B2 | 11/2013 | Zhou et al. | |
| 8,956,663 B2 | 2/2015 | Gordon et al. | |
| 10,258,567 B1 | 4/2019 | Krebs-Bensch | |
| 10,517,983 B2 | 12/2019 | Dhooge et al. | |
| 10,842,737 B1 | 11/2020 | Krebs-Bensch | |
| 10,857,094 B2 | 12/2020 | Weiss | |
| 2005/0220776 A1 | 10/2005 | Brondstad et al. | |
| 2008/0045909 A1 | 2/2008 | Fossel | |
| 2009/0226541 A1 | 9/2009 | Scholz et al. | |
| 2012/0052152 A1 * | 3/2012 | Armentrout | A23K 10/18 |
| | | | 426/2 |
| 2013/0101678 A1 | 4/2013 | Gordon et al. | |
| 2013/0243847 A1 * | 9/2013 | McDonald | A61L 15/20 |
| | | | 424/445 |
| 2014/0303183 A1 | 10/2014 | Okamoto | |
| 2018/0235987 A1 | 8/2018 | von Maltzahn et al. | |
| 2019/0307817 A1 * | 10/2019 | Fichorova | C12N 1/205 |
| 2019/0314340 A1 | 10/2019 | McDonald et al. | |

FOREIGN PATENT DOCUMENTS

| | | | | |
|---|---|---|---|---|
| EP | 1575628 | 9/2005 | | |
| WO | 84/04675 | 12/1984 | | |
| WO | 2010099182 | 9/2010 | | |
| WO | WO-2018125904 A1 * | 7/2018 | ............. | A01N 43/50 |

OTHER PUBLICATIONS

Holst et al. Journal of Clinical Microbiology, vol. 28, No. 9, Sep. 1990, p. 2035-2039.*
Cleveland Clinic. Bacterial Vaginosis. https://my.clevelandclinic.org/health/diseases/3963-bacterial-vaginosis retrieved Oct. 6, 2023.*
Dobaria et al. East and Central African Journal of Pharmaceutical Scienced vol. 10 (2007) 3-13.*
Sobel Jack D. et al., Division of Infectious Diseases, Department of Medicine, Wayne State University School of Medicine, The Detroit Medical Center, 1997; vol. 24, pp. 649-652; "Treatment of Torulopsis glabrata Vaginitis: Retrospective Review of Boric Acid Therapy"; https://academic.oup.com/cid/article-abstract/24/4/649/439957.
Bradshaw Catriona S. et al., Bradshaw and Brotman BMC Infectious Diseases; Making inroads into improving treatment of bacterial vaginosis—striving for long-term cure, 2015, 15:292.
"Voni Dust Vaginal Odor Eliminator Powder—Medical-Grade Boric Acid for Yoni PH Balance—All-Natural Intimate Feminine Health", https://www.Amazon.com.
Bradshaw Catriona S. et al., Journal of Infectious Diseases, High Recurrence Rates of Bacterial Vaginosis over the Course of 12 Months after Oral Metronidazole Therapy and Factors Associated with Recurrence; 2006; vol. 193; pp. 1478-1486.
Koumans, Emilia H. et al., Sexually Transmitted Diseases; "The Prevalence of Bacterial Vaginosis in the United States, 2001-2004; Associations with Symptoms, Sexual Behaviors, and Reproductive Health", Nov. 2007; vol. 34, No. 11, pp. 864-869.

(Continued)

*Primary Examiner* — Oluwatosin A Ogunbiyi (74) *Attorney, Agent, or Firm* — Bradley Arant Boult Cummings LLP (57) ABSTRACT

Compositions and methods for treatment and prevention of vaginal infections where the compositions include creatinine, such as protonated creatinine or creatinine salts, and optionally one or more weak acids, such as boric acid. The compositions may be used to treat and/or prevent a vaginal infection, such as bacterial vaginosis, to prevent recurrence of a vaginal infection, to treat and/or prevent a sexually transmitted disease (STD) or sexually transmitted infection (STI), and reduce the incidence and/or risk of a subject transmitting a STI or STD.

15 Claims, 2 Drawing Sheets

(56) References Cited

OTHER PUBLICATIONS

Bradshaw Catriona S. et al., PLoS One, "Prevalent and Incident Bacterial Vaginosis Are Associated with Sexual and Contraceptive Behaviours in Young Australian Women", Mar. 2013, vol. 8, Issue 3, e57688.
Chico, R. Matthew et al., JAMA, Prevalence of Malaria and Sexually Transmitted and Reproductive Tract Infections in Pregnancy in Sub-Saharan Africa, 2012, vol. 307, No. 19, pp. 2079-2086.
Sobel, J.D. et al., The Journal of Infectious Diseases, "Long-Term Follow-Up of Patients with Bacterial Vaginosis Treated with Oral Metronidazole and Topical Clindamycin", 1993, vol. 167, pp. 783-784.
International Search Report and Written Opinion dated Nov. 12, 2021 of corresponding International Patent Application No. PCT/US21/39769.
Prutting, S.M. et al., Infectious Diseases in Obstetrics and Gynecology; Boric Acid Vaginal Suppositories: A Brief Review, 1998, vol. 6, pp. 191-194.
Reagecon document, "How can the pH of a non-aqueous liquid be measured", accessible at https://knowledge.reagecon.com/faq/how-can-the-ph-of-a-non-aqueous-liquid-be-measured/#-text=The%20pH%20scale%20is%20defined.measurement%20in%20non%2Daqueous%20systems, Feb. 8, 2023 (Year: 2023).
Yilmaz, Minimum inhibitory and minimum bactericidal concentrations of boron compounds against several bacterial strains, Turkish Journal of Medical Sciences, Vo. 42, 2012, pp. 1423-1429.
International Search Report and Written Opinion dated Dec. 8, 2021 of corresponding Patent Application No. PCT/US2021/039934.
U.S. Statutory Invention Registration No. H672 published on Sep. 5, 1989 entitled "Stable Antifungal Capsule Formulation".
Extended European Search Report dated Jun. 13, 2024 of corresponding European Patent Application No. 21834437.2.

\* cited by examiner

COMPOSITIONS AND METHODS FOR TREATMENT OF VAGINAL INFECTIONS

FIELD OF THE INVENTION

The present invention generally relates to compositions of creatinine, such as protonated creatinine or creatinine salts, and optionally, a weak acid, and their use to treat or prevent vaginal and sexually transmitted infections.

BACKGROUND OF THE INVENTION

Bacterial vaginosis (BV) is a common vaginal infection that affects reproductive-aged women worldwide. Prevalence estimates range from 12% in Australian women (Bradshaw C S, et al. *PLoS One* 2013; 8:e57688) and 29% in North American women (Koumans E H, et al. *Sex Transm Dis* 2007; 34:864-9) to >50% of women affected in East/Southern Africa (Chico R M, et al. *JAMA* 2012; 307:2079-86). BV is characterized by the loss of normal vaginal flora, predominantly hydrogen peroxide-producing *Lactobacillus*, and overgrowth of other bacteria in the vaginal fluid. BV is associated with a number of health problems including an increased risk of acquiring the human immunodeficiency disease (HIV); an increased risk of HIV viral shedding among HIV infected women; an increased risk of acquiring other sexually transmitted infections (STIs) such as gonorrhea, trichomoniasis, *chlamydia*, and herpes simplex virus type 2; an increased risk of developing urinary tract infections (UTIs); and an increased risk of miscarriage, preterm labor, preterm delivery, and postpartum complications in pregnant women.

There are a variety of treatment and therapy options currently on the market for treating vaginal infections such as BV. For example, a common therapy option is the use of boric acid. Boric acid is a weak, tribasic Lewis acid of boron and is often used to treat vaginal infections. Intravaginal boric acid is used in a dosage of 600 mg daily for at least 14 days. However, boric acid treatments alone are slow and take a long period of time to achieve therapeutic results.

Vaginal infections, including BV, can also be treated with antibiotics such as metronidazole, clindamycin, and tinidazole. However, the recommended antibiotics kill not only the harmful bacteria, but also useful bacteria in the vaginal flora that work to keep other germs in check. This means that antibiotic treatment can sometimes end up causing a vaginal yeast infection (*candida* fungus). The antibiotics also have detrimental side effects. For instance, metronidazole tablets leave behind a metallic taste and can cause nausea and vomiting. Moreover, while short-term cure rates following recommended regimens of antibiotics are high, studies with extended follow-up show that recurrence rates in excess of 50% occur within 6-12 months (Sobel J D, et al. *J Infect Dis* 1993; 167:783-4; Bradshaw C S, et al. *J Infect Dis* 2006; 193:1478-89). As such, patients taking antibiotics often experience recurrent and virulent infections. Furthermore, the overuse of antibiotics promotes antibiotic resistance, which can lead to more serious illnesses, longer recovery times, and more doctor visits.

Accordingly, there remains a need in the art for a more effective and longer lasting treatment for vaginal infections, such as BV, that provides immediate results and fewer side effects.

SUMMARY OF THE INVENTION

The problems expounded above, as well as others, are addressed by the following inventions, although it is to be understood that not every embodiment of the inventions described herein will address each of the problems described above.

In one embodiment, a method for treatment and prevention of a vaginal infection in a subject is provided, the method including administering to the subject an effective amount of a composition including protonated creatinine, a protonated creatinine salt, or combinations thereof, wherein the protonated creatinine, protonated creatinine salt, or combination thereof is present in the composition in an amount of about 20 µg to about 1000 mg, preferably about 33 µg to about 600 mg. In one embodiment, the composition may further include a weak acid having a pH value of about 3 to about 7, such as boric acid, lactic acid, ascorbic acid, acetic acid, citric acid, hydrogen sulfide, propionic acid, or carbonic acid. For example, the weak acid may be boric acid. In another embodiment, the vaginal infection is selected from bacterial vaginosis, vaginal candidiasis, urinary tract infection, pelvic inflammatory disease, extra-cellular *chlamydia*, gonococcal vaginitis, viral vaginitis, or non-infectious vaginitis. For instance, the vaginal infection may be bacterial vaginosis. In still another embodiment, the composition is formulated as a vaginal suppository, vaginal capsule, vaginal tablet, coated tampon, or coated condom. In yet another embodiment, the composition is formulated as a gel, lotion, spray, ointment, cream, paste, lubricant, or emulsion. In another embodiment, the composition includes a pharmaceutically acceptable carrier suitable as a transmucosal carrier and the composition is formulated for vaginal transmucosal administration.

In some embodiments, the composition further includes a probiotic, a prebiotic, or combinations thereof. For example, the probiotic may be of the *Lactobacillus* species. The prebiotic may be selected from short chain fructo-oligosaccharides, inulin, lactulose, galactooligosaccharide, isomaltooligosaccharide, soy-oligosaccharide, or xylo-oligosaccharide.

In other embodiments, a method for treatment and prevention of a sexually transmitted infection (STI) or sexually transmitted disease (STD) in a subject is provided, the method including administering to the subject an effective amount of a composition including protonated creatinine, a protonated creatinine salt, or combinations thereof, wherein the protonated creatinine, protonated creatinine salt, or combination thereof is present in the composition in an amount of about 33 µg to about 600 mg. In this embodiment, the STI or STD is selected from the group consisting of extracellular *chlamydia*, gonorrhea, genital *mycoplasma*, trichomoniasis, herpes simplex virus, and infections caused by human papillomavirus (HPV). In another embodiment, the composition is formulated as a vaginal suppository, vaginal capsule, or vaginal tablet. In still another embodiment, the protonated creatinine, protonated creatinine salt, or combination thereof is present in the composition in an amount of about 10 mg to about 300 mg.

In still other embodiments, a vaginal suppository is provided, the vaginal suppository including a composition including protonated creatinine, protonated creatinine salt, or combinations thereof, wherein the amount of the protonated creatinine, protonated creatinine salt, or combination thereof is about 33 µg to about 600 mg. In one embodiment, the composition may further include a probiotic, a prebiotic, or combinations thereof. For example, the probiotic may be of the *Lactobacillus* species. In another embodiment, the prebiotic is selected from the group consisting of short chain fructo-oligosaccharides, inulin, lactulose, galactooligosaccharide, isomalto-oligosaccharide, soy-oligosaccharide, and xylo-oligosaccharide.

BRIEF DESCRIPTION OF THE DRAWINGS

Further features and advantages can be ascertained from the following detailed description that is provided in connection with the drawings described below.

DETAILED DESCRIPTION OF THE INVENTION

Definitions

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well-known functions or constructions may not be described in detail for brevity or clarity.

As used herein, the singular forms "a," "an," and "the" include plural referents unless the context clearly dictates otherwise. For example, reference to "the method of treatment" includes reference to equivalent steps and methods known to those skilled in the art, and so forth.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments, the values may range in value either above or below the stated value in a range of approx. +/−5%; in other embodiments, the values may range in value either above or below the stated value in a range of approx. +/−2%; in other embodiments, the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "administering" or "administration" include acts such as prescribing, dispensing, giving, or taking a substance such that what is prescribed, dispensed, given, or taken actually contacts the patient's body externally or internally (or both). It is specifically contemplated that instructions or a prescription by a medical professional to a subject or patient to take or otherwise self-administer a substance is an act of administration.

The terms "prevention," "prevent," "preventing," "suppression," "suppress," and "suppressing" as used herein refer to a course of action initiated prior to the onset of a clinical manifestation of a disease state or condition so as to reduce the likelihood or severity of such clinical manifestation of the disease state or condition. Such reduction of the likelihood or severity need not be absolute to be useful. The terms also refer to inhibiting the full development of a disease state or condition in a subject who is at risk of developing the disease state or condition.

The terms "treat," "treating," or "treatment" refers to alleviating, reducing, or inhibiting one or more symptoms or physiological aspects of a disease, disorder, syndrome, or condition. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The terms "alleviate" or "alleviation" refer to a lessening of the severity of one or more symptoms.

The terms "in need of treatment" and "in need of prevention" as used herein refer to a judgment made by a caregiver that a patient requires or will benefit from treatment or prevention. This judgment is made based on a variety of factors that are in the realm of a caregiver's expertise, but that includes the knowledge that the patient is ill, or will be ill, as the result of a condition that is treatable by a method or composition of the present disclosure.

The terms "individual," "subject," and "patient" are used interchangeably herein, and refer to any animal, including mammals, such as mice, rats, other rodents, rabbits, dogs, cats, swine, cattle, sheep, horses, primates, and humans.

The terms "inhibit," "decrease," and/or "reduce the likelihood of" (and like terms) generally refers to the act of reducing, either directly or indirectly, a function, activity, or behavior relative to the natural, expected, or average or relative to current conditions. It is understood that this is typically in relation to some standard or expected value, in other words it is relative, but that it is not always necessary for the standard or relative value to be referred to. Such terms can include complete inhibition, complete reduction, or elimination of the likelihood of a function, activity, or behavior relative to the natural, expected, or average or relative to current conditions.

The term "pharmaceutically-acceptable carrier" refers to one or more compatible solid or liquid fillers, diluents, or encapsulating substances that does not cause significant irritation to a human or other vertebrate animal and does not abrogate the biological activity and properties of the administered compound. Such carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. However, the nature of the pharmaceutically acceptable carrier may differ depending on the particular dosage form employed and other characteristics of the composition. The pharmaceutically acceptable carriers can include polymers and polymer matrices.

The terms "effective amount" or "therapeutically effective amount" as used herein refer to an amount of an agent, either alone or as a part of a pharmaceutical composition, that is capable of having any detectable, positive effect on any symptom, aspect, or characteristics of a disease state or condition. Such effect need not be absolute to be beneficial.

Compositions

In one embodiment, compositions including an effective amount of creatinine, such as protonated creatinine or creatinine salts, for treating or preventing vaginal infections are disclosed. In another embodiment, compositions including an effective amount of creatinine, such as protonated creatinine or creatinine salts, and one or more weak acids for treating or preventing vaginal infections are disclosed. Without being bound by any particular theory, it is believed that the disclosed compositions are able to kill bacteria and stabilize and restore vaginal pH to approximately 3.5 to 4.5, which results in an effective treatment for vaginal infections. The disclosed compositions also provide faster results and fewer side effects when compared to conventional treatments, such as the use of boric acid alone or antibiotics like metronidazole, clindamycin, and tinidazole.

In one embodiment, the disclosed compositions include creatinine. For example, the compositions according to the present disclosure may include a compound having the structure of formula (I):

(I)

In another embodiment, the disclosed compositions include a protonated form of creatinine. Protonated creatinine may be represented by the resonance structures of formula (IIa) and formula (IIb):

Protonated creatinine can be made by converting the electronically neutral creatinine molecule to the protonated form. In this embodiment, the protonated form of creatinine can be made by mixing creatinine with an acid or by adding creatinine to an aqueous medium having a pH below about 6.5, preferably in the range of about 5.0 to about 5.5. Suitable acids for converting creatinine to protonated creatinine include both organic acids, such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid, as well as inorganic acids, such as hydrochloric acid, hydrobromic acid, sulfuric acid, nitric acid, phosphoric acid, and the like.

In another embodiment, protonated creatinine can be made by converting a protonated precursor of creatinine to protonated creatinine. For example, alkyl esters of creatine, such as creatine ethyl ester ("CEE") (shown as formula (III) below), can be provided as an acid addition salt using any of the organic acids or inorganic acids mentioned above, and will readily convert in aqueous media to protonated creatinine salts (shown as formula (IIIa) and formula (IIIb) below):

where X is an anion such as a halide, e.g., chloride, or an organic anion such as acetate, succinate, oxalate, or the like.

In this embodiment, the compositions of the present invention may also include a protonated creatinine salt. For example, creatinine salts contemplated by the present invention include, but are not limited to, creatinine hydrochloride (HCl), creatinine nitrate, creatinine malate, creatinine gluconate, creatinine zinc chloride, creatinine citrate, and mixtures thereof. In one embodiment, the compositions of the present invention include creatinine HCl.

In yet another embodiment, the compositions of the present invention may include a combination of protonated creatinine and creatinine salt. For example, the compositions of the present invention may include protonated creatinine and creatinine HCl. In another embodiment, the compositions of the present invention may include a combination of two or more creatinine salts. For instance, the compositions of the present invention may include creatinine HCl and creatinine nitrate.

The protonated creatinine and creatinine salts of the present invention may be produced by any suitable method known to one of ordinary skill in the art. Preparations of the protonated creatinine and creatinine salts for use with the present invention are preferably at least about 80 percent pure, preferably at least about 95 percent pure, more preferably at least about 97 percent pure, and even more preferably at least about 99 percent pure. The term "pure" as used herein refers to the lack of impurities in the preparation.

In some embodiments, the disclosed compositions may also include one or more weak acids. As used herein, the term "weak acid" refers to an acid that is partially dissociated into its ions in an aqueous solution or water and has a pH value at 1 mM of less than 7. In one embodiment, the weak acid has a pH at 1 mM of about 2 to less than about 6.5. In another embodiment, the weak acid has a pH at 1 mM of about 3 to about 6.3. In still another embodiment, the weak acid has a pH at 1 mM of about 3 to about 6.2. In yet another embodiment, the pH of the weak acid at 1 mM is about 3.05 to about 6.15. For example, the pH of the weak acid at 1 mM is about 3.5 to 6.2. In one embodiment, the weak acid may also have a pKa value in the range of about 4 to about 9.5. In another embodiment, the weak acid has a pKa value in the range of about 7 to about 9.5. For example, the weak acid may have a pH at 1 mM of about 4.9 to about 6.12 and a pKa value of about 7 to about 9.3.

Suitable weak acids contemplated by the present disclosure include, but are not limited to, boric acid, hydrogen sulfide, ethanoic/acetic acid, lactic acid, citric acid, tartaric acid, ascorbic acid, maleic acid, propionic acid, carbonic acid, and combinations thereof.

In some embodiments, the disclosed compositions include boric acid as the weak acid. Boric acid, also known as hydrogen borate, is a weak, tribasic Lewis acid of boron having the structure of formula (II):

(II)

The boric acid may be produced by any suitable method known to one of ordinary skill in the art. In one embodiment, the boric acid is prepared by treating borax with nitric acid in accordance with the following:

$$Na_2B_4O_7 \cdot 10H_2O + 2HNO_3 \rightarrow 4H_3BO_3 + 2NaNO_3 + 5H_2O$$

For example, borax ($Na_2B_4O_7 \cdot 10H_2O$) may be dissolved in boiling distilled water and filtered. An excess of nitric acid is then added to the hot filtrate. After crystals of boric acid form, they are collected by filtration and washed with cold distilled water. The boric acid may then be purified by redissolving the washed crystals in boiling distilled water. In another embodiment, boric acid is prepared by treating borax with hydrochloric acid.

In other embodiments, the compositions of the present invention include propionic acid as the weak acid. The propionic acid may be produced by any suitable method known to those of ordinary skill in the art. For example, the propionic acid may be prepared by hydrocarboxylation of ethylene using nickel carbonyl as a catalyst or aerobic oxidation of propionaldehyde. In still other embodiments, the compositions of the present invention include carbonic acid, which may be produced by any suitable method known to those of ordinary skill in the art. For example, the carbonic acid may be prepared by reacting calcium carbonate and hydrochloric acid in the presence of water.

The compositions of the present invention may include two or more weak acids. For example, in this aspect, the compositions may include boric acid and a second weak acid, e.g., citric acid. In still another embodiment, the compositions may include three or more weak acids.

In still another embodiment, the disclosed compositions may include an antifungal agent. Suitable antifungal agents include, but are not limited to, tovaquone, griseofulvin, nystatin, polymyxin B, amphotericin B, terbinafine, and imidazole and triazole compounds such as butoconazole, clotrimazole, econazole, fluconazole, isoconazole, itraconazole, ketoconazole, miconazole, oxiconazole, ravuconazole, saperconazole, sertaconazole, sulconazole, terconazole, tioconazole, voriconazole, pharmaceutically acceptable salts and esters thereof, and mixtures thereof.

In yet another embodiment, the disclosed compositions may include a probiotic. Suitable probiotics for use with the present disclosure are any number of defined viable microorganisms that reach the female genital tract in an active state and thus exert positive health effects. In one embodiment, a species of *Lactobacillus* is employed as the probiotic. Suitable species of *Lactobacillus* include, but are not limited to, *Lactobacillus iners, Lactobacillus crispatus, Lactobacillus gasseri, Lactobacillus jensenii, Lactobacillus rhamnosus* GG, *Lactobacillus reuteri* (RC-14), *Lactobacillus acidophilus, Lactobacillus delbrueckii, Lactobacillus helveticus, Lactobacillus salivarius, Lactobacillus casei, Lactobacillus paracasei, Lactobacillus curvatus, Lactobacillus plantarum, Lactobacillus sakei, Lactobacillus brevis, Lactobacillus buchneri, Lactobacillus fermentum, Bifidobacterium lactis, B. longum, Lactobacillus acidophilus* LA02, *Lactobacillus buchneri* Lb26, *Lactobacillus fermentum* ME-3, *Lactobacillus salivarius* subsp. *salivarius* CRL 1328, *Lactobacillus* crispatus CRL 1266, *Lactobacillus paracasei* subsp. *paracasei* CRL 1289, *Lactobacillus gasseri* CRL 1259, *Lactobacillus plantarum* LP02, *Lactobacillus delbrueckii* subsp. *bulgaricus* LDB-1, and combinations thereof. In another embodiment, the probiotic employed includes *Bifidobacterium* and certain strains of *Lactobacillus casei* or the *Lactobacillus acidophilus*-group. In yet another embodiment, the probiotic employed includes any of the above species of *Lactobacillus* and *Escherichia coli* strain Nissle 1917, *Enterococcus faecium* SF68, the probiotic yeast *Saccharomyces boulardii*, or combinations thereof.

In still another embodiment, the disclosed compositions may include a prebiotic. Prebiotics differ from probiotics in that they act as a fertilizer for the good bacteria that is already present in the body. In addition, whereas probiotics are live bacteria that are susceptible to heat, acid, and time, prebiotics are indigestible dietary fibers that are not destroyed in the body because they are not susceptible to heat, cold, acid, or time. Suitable prebiotics for use with the present disclosure are any number of selectively fermented ingredients that allows specific changes, both in the composition and/or activity in the female genital tract. Examples include, but are not limited to, bifidogenic oligosaccharides such as fructo-oligosaccharide, inulin, lactulose, galactooligosaccharide, isomalto-oligosaccharide, soy-oligosaccharide, and xylo-oligosaccharide. In one embodiment, the prebiotic includes short chain fructo-oligosaccharides (scFOS). The scFOS may be derived from beet or sugar cane.

Formulations

In one embodiment, the disclosed compositions are in the form of pharmaceutical compositions. For example, pharmaceutical compositions are provided including therapeutically effective amounts of protonated creatinine, creatinine salts, or combinations thereof, and optionally pharmaceutically acceptable diluents, preservatives, solubilizers, emulsifiers, adjuvants, excipients, and/or carriers. In other embodiments, pharmaceutical compositions are provided including therapeutically effective amounts of protonated creatinine or creatinine salts and one or more weak acids, and optionally pharmaceutically acceptable diluents, preservatives, solubilizers, emulsifiers, adjuvants, excipients, and/or carriers. The disclosed compositions may further include agents which improve the solubility, half-life, absorption, etc. of the protonated creatinine or creatinine salts and one or more weak acids. Furthermore, the disclosed compositions may further include agents that attenuate undesirable side effects and/or decrease the toxicity of the protonated creatinine or creatinine salts and one or more weak acids. Examples of such agents are described in a variety of texts, such as, but not limited to, Remington: The Science and Practice of Pharmacy (20th Ed., Lippincott, Williams & Wilkins, Daniel Limmer, editor).

The pharmaceutical compositions may be formulated to be provided to the subject in any method known in the art. For instance, the pharmaceutical compositions may be formulated for administration by parenteral (for example, intramuscular, intraperitoneal, intravitreally, intravenous (IV), or subcutaneous injection), transmucosal (for example, vaginal), or transdermal routes of administration and can be formulated in dosage forms appropriate for each route of administration.

In one embodiment, the disclosed compositions are administered in solid form. Suitable solid forms include tablets, capsules, pills, pellets, powders, granules, or incorporation of the material into particulate preparations of polymeric compounds such as polylactic acid, polyglycolic acid, or into liposomes. In another embodiment, the disclosed compositions are administered in liquid dosage form. Examples of liquid dosage forms for vaginal administration include pharmaceutically acceptable emulsions, solutions, suspensions, and syrups, which may contain other components including inert diluents; preservatives; binders; stabilizers; adjuvants such as wetting agents, emulsifying and suspending agents; and perfuming agents.

Controlled release formulations, for example, delayed release or extended release formulations, may also be desirable. For example, the disclosed compositions may be encapsulated in a soft or hard gelatin or non-gelatin capsule or dispersed in a dispersing medium to form a suspension or syrup. In another embodiment, the disclosed compositions may be lipid-encapsulated. The particles can be formed of the composition and a controlled release polymer or matrix. Alternatively, the particles can be coated with one or more controlled release coatings (for example, delayed release or extended release coatings) prior to incorporation into the finished dosage form. In still another embodiment, the disclosed compounds may be dispersed in a matrix material, which gels or emulsifies upon contact with an aqueous medium. Such matrices may be formulated as tablets or as fill materials for hard and soft capsules.

In some embodiments, the disclosed compositions are preferably applied directly into the vaginal cavity, and therefore, the disclosed compositions are formulated for topical application. Topical dosage forms include, but are not limited to, gels, lotions, sprays, ointments, creams, pastes, lubricants, and emulsions, containing the disclosed compositions. In one embodiment, the disclosed compositions are formulated as a gel, for example, a vaginal suppository gel, that may be applied directly into the vaginal cavity.

The topical dosage forms can be admixed with penetration enhancers and a variety of carrier materials well known in the art, such as alcohols, aloe vera gel, allantoin, glycerine, vitamin A and E oils, mineral oil, coconut oil, PPG2 (polypropylene glycol 2) myristyl propionate, and the like.

In some embodiments, the disclosed compositions may be formulated for transmucosal administration. Transmucosal administration refers to a route of administration in which the composition is diffused through the mucous membrane. For instance, the disclosed compositions may be formulated for vaginal transmucosal administration. Formulations for administration to the mucosa will typically be spray dried drug particles, which may be incorporated into, for example, tablets, hard and soft gelatin capsules, suspensions, emulsions, creams, lotions, sprays, foams, ointments, pastes, lubricants, tampons, vaginal rings, douches, pessaries, or suppositories.

For example, the disclosed compositions may be in the form of a vaginal suppository. In this aspect, the suppository may be torpedo or bullet shaped, round, an elongated oval, teardrop shaped, or cone shaped. The vaginal suppository may be lipophilic based or hydrophilic based. In this regard, vaginal suppositories for use with the present invention may be made of cocoa butter, coconut oil, glycerinated gelatin, hydrogenated vegetable oils and hard fats, polyethylene glycols (PEGs), fatty acid esters of PEG, and combinations thereof. In one embodiment, such as with lipophilic fat-based suppositories, the vaginal suppository melts at body temperature to release the composition of the invention to the body. Without being bound to any particular theory, lipophilic fat-based suppositories may be most useful in connection with delivering the compositions of the invention when vaginal dryness is an issue. In contrast, since the hydrophilic water-based suppositories are unaffected by body temperature and use the body fluids to dissolve the suppository to release the composition to the body, such suppository may be most useful when vaginal dryness is not an issue.

In another embodiment, the disclosed compositions may be in the form of a vaginal capsule. In still another embodiment, the disclosed compositions may be in the form of a vaginal tablet. In yet another embodiment, the disclosed compositions may be in the form of a suspension. In another embodiment, the disclosed compositions may be administered in the form of a tampon coated with the disclosed composition. In still another embodiment, the disclosed compositions may be administered in the form of a condom coated with the disclosed composition. In yet another embodiment, the disclosed compositions may be administered as a vaginal lube. In another embodiment, the disclosed compositions may be administered using a bellows bottle.

The compositions may also be administered in the form of an aqueous spray. In one embodiment, the spray may include an effective amount of protonated creatinine, creatinine salts, or combinations thereof. In another embodiment, the spray may include an effective amount of protonated creatinine, creatinine salts, or combinations thereof, and one or more weak acids. In addition, the spray may include additional components such as excipients, fragrances, buffering agents, and the like. For example, in one embodiment, the spray includes protonated creatinine, a buffering agent, and water. In another embodiment, the spray may include at least one weak acid, protonated creatinine, a buffering agent, and water.

To form a pharmaceutically acceptable composition suitable for administration, such compositions will contain therapeutically effective amounts of protonated creatinine or creatinine salts. The disclosed compositions are administered to a subject in an amount sufficient to deliver a therapeutically effective amount of the protonated creatinine, creatinine salts, or combinations thereof so as to be effective in the treatment and prevention of the methods disclosed herein. In other embodiments, pharmaceutically acceptable compositions will contain therapeutically effective amounts of protonated creatinine, creatinine salts, or combinations thereof, and one or more weak acids. The disclosed compositions are administered to a subject in an amount sufficient to deliver a therapeutically effective amount of the protonated creatinine or creatinine salts and one or more weak acids so as to be effective in the treatment and prevention of the methods disclosed herein. The precise dosage may vary according to a variety of factors such as, but not limited to, the subject's condition, weight, sex, and age. The selected dosage also depends upon the desired therapeutic effect, on the route of administration, and on the duration of the treatment desired.

For the disclosed compositions, each dose/treatment includes an effective amount of protonated creatinine, creatinine salts, or combinations thereof. In one embodiment, the effective amount is about 20 µg to about 1000 mg. In another embodiment, the dosage of protonated creatinine or creatinine salts is about 25 µg to about 800 mg. In still another embodiment, the dosage of protonated creatinine or creatinine salts is about 33 µg to about 600 mg. In yet another embodiment, the dosage of protonated creatinine or creatinine salts is about 75 µg to about 400 mg. In another embodiment, the dosage of protonated creatinine or creatinine salts is about 10 mg to about 300 mg.

In some embodiments, the composition also includes an effective amount of the one or more weak acids. In one embodiment, the effective amount/dosage of the weak acid ranges from about 100 mg to about 1200 mg per day. In another embodiment, the dosage of the weak acid is about 300 mg to about 900 mg per day. In still another embodiment, the dosage of the weak acid is about 500 mg to about 700 mg per day. In yet another embodiment, the dosage of the weak acid is about 200 mg to about 500 mg. For example, the dosage of the weak acid may be about 600 mg.

In this embodiment, a daily dose or application of the compositions of the invention may include, for example, about 33 µg to about 600 mg protonated creatinine and about 300 mg to about 900 mg boric acid. In another embodiment, the daily dose or application of the composition of the invention may include about 75 µg to about 400 mg protonated creatinine and about 500 mg to about 700 mg boric acid. In yet another embodiment, the daily dose or application of the composition of the invention may include about 10 mg to about 300 mg protonated creatinine and about 500 mg to about 700 mg boric acid.

The other components of the disclosed compositions, for example, the antifungal agent, the probiotic, and/or the prebiotic may be present in the compositions in an amount sufficient to deliver a therapeutically effective amount so as to be effective in the treatment and prevention of the methods disclosed herein. In one embodiment, the amount of antifungal agent present in the compositions may be such that the antifungal agent represents in the range of about 0.25 mol % to about 4 mol % of the combination of the antifungal agent and the protonated creatinine or creatinine salts. In another embodiment, the amount of antifungal agent present in the compositions may be such that the antifungal agent represents in the range of about 0.5 mol % to about 30 mol % of the combination of the antifungal agent and the protonated creatinine or creatinine salts. In still another embodiment, the amount of antifungal agent present in the compositions may be such that the antifungal agent represents in the range of about 0.5 mol % to about 20 mol % of the combination of the antifungal agent and the protonated creatinine or creatinine salts. In yet another embodiment, the amount of antifungal agent present in the compositions may be such that the antifungal agent represents in the range of about 0.5 mol % to about 10 mol % of the combination of the antifungal agent and the protonated creatinine or creatinine salts. For example, the antifungal agent may be present in the composition in the amount of about 1 mol % to about 6 mol %.

In some embodiments, the probiotic may be present in the compositions in an amount of about 25 mg to about 600 mg. In another embodiment, the probiotic may be present in the compositions in an amount of about 40 mg to about 500 mg. In still another embodiment, the probiotic may be present in the compositions in an amount of about 75 mg to about 400 mg. However, without being bound by any particular theory, use of lesser amounts of probiotics remain effective if applied directly to/in the vaginal cavity. In this aspect, the composition may include about 5 mg to about 200 mg probiotic. For example, the probiotic may be present in the composition in an amount of about 5 mg to about 150 mg. In one embodiment, the composition includes about 5 mg to about 100 mg of probiotic.

In other embodiments, the prebiotic may be present in the compositions in an amount of about 25 mg to about 200 mg. In another embodiment, the prebiotic may be present in the compositions in an amount of about 50 mg to about 175 mg. In still another embodiment, the prebiotic may be present in the compositions in an amount of about 80 mg to about 140 mg.

Methods of Use

The disclosed compositions can be used, for example, to treat and/or prevent a vaginal infection, such as BV, to prevent recurrence of a vaginal infection, to treat and/or prevent a sexually transmitted disease (STD) or sexually transmitted infection (STI), and reduce the incidence and/or risk of a subject transmitting a STI or STD.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or an average determined from measuring the symptom, pharmacologic, or physiologic indicator in one or more subjects that do not have the disease or condition to be treated (for example, healthy subjects). In some embodiments, the effect of the treatment is compared to a conventional treatment that is known in the art.

One embodiment provides a method of treatment and/or prevention of a vaginal infection in a subject. The vaginal infection may include, for instance, bacterial vaginosis, vaginal candidiasis, urinary tract infection, pelvic inflammatory disease, gonococcal vaginitis, viral vaginitis, non-infectious vaginitis, and similar conditions that involve an elevated pH and/or a disturbed microbiota in the urogenital tract. By an "elevated pH," it is meant a pH above 4.5. In one embodiment, the present disclosure provides a method of treatment and/or prevention of bacterial vaginosis. The method may include administering to a subject in need of treatment an effective amount of the disclosed compositions. In this embodiment, the disclosed compositions are effective to kill bacteria and lower an elevated vaginal pH to below 5, preferably below 4.7, more preferably below 4.5, and even more preferably below 4.0, to a normal vaginal pH, and thereby restore vaginal pH and treat vaginal infections such as bacterial vaginosis. For example, the disclosed compositions are effective to kill *Gardnerella vaginalis* (*G. vaginalis*), which is a species of bacteria that can contribute to the development of bacterial vaginosis. In other embodiments, the disclosed compositions are effective to kill *Mobiluncus mulieris* (*M. mulieris*), which is a species of bacteria associated with bacterial vaginosis.

In treating vaginal infections, such as bacterial vaginosis, the disclosed compositions advantageously provide faster results and fewer side effects when compared to conventional treatments, such as the use of boric acid alone or antibiotics like metronidazole, clindamycin, and tinidazole. For instance, in one embodiment, one or more symptoms of the vaginal infection, such as abnormal vaginal discharge, vaginal itching, vaginal odor, and burning during urination, are alleviated within about 12 hours after administration of the disclosed compositions. In another embodiment, one or more symptoms of the vaginal infection are alleviated within about 24 hours after administration. In still another embodiment, one or more symptoms of the vaginal infection are alleviated within about 36 hours after administration. In yet another embodiment, one or more symptoms of the vaginal infection are alleviated within about 48 hours after administration.

The disclosed compositions are also advantageous in preventing recurrence of the vaginal infection. One embodiment provides for a method of preventing recurrence of a vaginal infection, such as bacterial vaginosis. As used herein, "preventing recurrence of a vaginal infection" refers to the prevention of a new vaginal infection after discontinuation of treatment of the disclosed compositions for a previous vaginal infection and where the infectious agent is not reintroduced. The method may include administering to a subject in need thereof an effective amount of the disclosed compositions. In one embodiment, the disclosed compositions prevent recurrence of a vaginal infection for at least one month after the final administration. In another embodiment, the disclosed compositions prevent recurrence of a vaginal infection for at least three months after the final administration. In yet another embodiment, the disclosed compositions prevent recurrence of a vaginal infection for at least six months after the final administration. In still another embodiment, the disclosed compositions prevent recurrence of a vaginal infection for at least one year after the final administration.

In some embodiments, the rate of recurrence of a new vaginal infection after administration of the disclosed compositions is reduced by at least 30 percent. In another embodiment, the rate of recurrence of a new vaginal infection after administration of the disclosed compositions is reduced by at least 50 percent. In still another embodiment, the rate of recurrence of a new vaginal infection after administration of the disclosed compositions is reduced by at least 70 percent. In yet another embodiment, the rate of recurrence of a new vaginal infection after administration of the disclosed compositions is reduced by at least 90 percent. For example, the rate of recurrence of a new vaginal infection after administration of the disclosed compositions is reduced by at least 95 percent, preferably by at least 98 percent.

Another embodiment provides a method of treatment and/or prevention of a sexually transmitted infection (STI) or sexually transmitted disease (STD) in a subject. Examples of STIs and STDs that can be treated, prevented, or reduced by the disclosed compositions may include, for example, *chlamydia* (extracellular), gonorrhea, genital *mycoplasma*, trichomoniasis, herpes simplex virus, human immunodeficiency virus (HIV), and infections caused by human papillomavirus (HPV). The method may include administering to the subject an effective amount of the disclosed compositions.

In this embodiment, the disclosed compositions are effective to treat and/or prevent the STI or STD in the subject. For example, in some embodiments, one or more symptoms of *chlamydia*, such as abnormal vaginal discharge and burning during urination, are alleviated within about 12 hours after administration of the disclosed compositions. In another embodiment, one or more symptoms of *chlamydia* are alleviated within about 24 hours after administration. In still another embodiment, one or more symptoms of *chlamydia* are alleviated within about 36 hours after administration. In yet another embodiment, one or more symptoms of *chlamydia* are alleviated within about 48 hours after administration.

In other embodiments, one or more symptoms of gonorrhea, such as increased vaginal discharge, burning during urination, and vaginal bleeding between periods, are alleviated within about 12 hours after administration of the disclosed compositions. In another embodiment, one or more symptoms of gonorrhea are alleviated within about 24 hours after administration. In still another embodiment, one or more symptoms of gonorrhea are alleviated within about 36 hours after administration. In yet another embodiment, one or more symptoms of gonorrhea are alleviated within about 48 hours after administration.

Some embodiments provide a method of reducing the incidence and/or risk of a subject transmitting a STI or STD. Bacterial vaginosis may increase the risk of transmitting a STD, such as HIV, to a sexual partner. The method, which may include administering to a subject in need thereof an effective amount of the disclosed compositions, reduces the incidence rate of a subject transmitting a STI or STD to their partner by at least 20 percent. In another embodiment, the disclosed methods reduce the incidence rate of a subject transmitting a STI or STD to their partner by at least 40 percent. In still another embodiment, the disclosed methods reduce the incidence rate of a subject transmitting a STI or STD to their partner by at least 60 percent. In yet another embodiment, the disclosed methods reduce the incidence rate of a subject transmitting a STI or STD to their partner by at least 80 percent, preferably by at least 90 percent, and more preferably by at least 95 percent.

The treatment regime of the disclosed compositions can vary based on the condition, disorder, or disease to be treated. The duration of treatment can extend over several days or longer, depending on the condition, with the treatment continuing until the symptoms of the infection or disease are sufficiently reduced or eliminated. The progress of this therapy can be monitored by conventional techniques and assays, and may be used to adjust dosage to achieve a therapeutic effect.

In one embodiment, the duration of treatment is from about one day to about eight days. For example, the disclosed compositions are administered to a subject in need thereof over a time period of seven days. In another embodiment, the disclosed compositions are administered to the subject in need thereof over a time period of five days. In still another embodiment, the disclosed compositions are administered to the subject in need thereof over a time period of three days. In yet another embodiment, the disclosed compositions are administered to the subject in need thereof over a time period of two days. In another embodiment, the disclosed compositions are administered to the subject in need thereof over a single day.

The disclosed compositions may be administered on a daily basis. For example, the disclosed compositions may be administered to the subject once a day. In another embodiment, the disclosed compositions are administered to the subject at least twice a day. In still another embodiment, the disclosed compositions are administered to the subject at least three times a day.

The disclosed compositions can be administered to a subject in need thereof in combination or alternation with other therapies and therapeutic agents. In some embodiments, the disclosed compositions and the additional therapeutic agent are administered separately, but simultaneously, or in alternation. The disclosed compositions and the additional therapeutic agent can also be administered as part of the same composition. In other embodiments, the disclosed compositions and the additional therapeutic agent are administered separately and at different times, but as part of the same treatment regime.

Exemplary therapies and therapeutic agents include, but are not limited to, anti-inflammatory agents, cytokines, chemotherapeutic agents, radionuclides, other immunotherapeutics, enzymes, antifungals, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

EXAMPLES

The following non-limiting examples are merely illustrative of the preferred embodiments of the present invention and are not to be construed as limiting the invention, the scope of which is defined by the appended claims.

Example 1: Creatinine Hydrochloride Inhibited Growth of G. vaginalis

Formulations of creatinine hydrochloride were prepared in different concentrations to evaluate the effect on the inhibition of growth of G. vaginalis. Creatinine hydrochloride was used in varying concentrations ranging from 0.0625 mg/mL to 16 mg/mL. The minimum inhibitory concentration (MIC) for each solution was determined against G. vaginalis using two-fold dilutions and flat-bottom 96-well plates. For anaerobic bacteria, the MIC is the concentration where no growth, or the most significant reduction in growth is observed after 48-hour incubation (Clinical and Laboratory Standards Institute M11-A6: Methods for Antimicrobial Susceptibility Testing of Anaerobic Bacteria; Approved Standard—$6^{th}$ Edition).

Figure 1A:
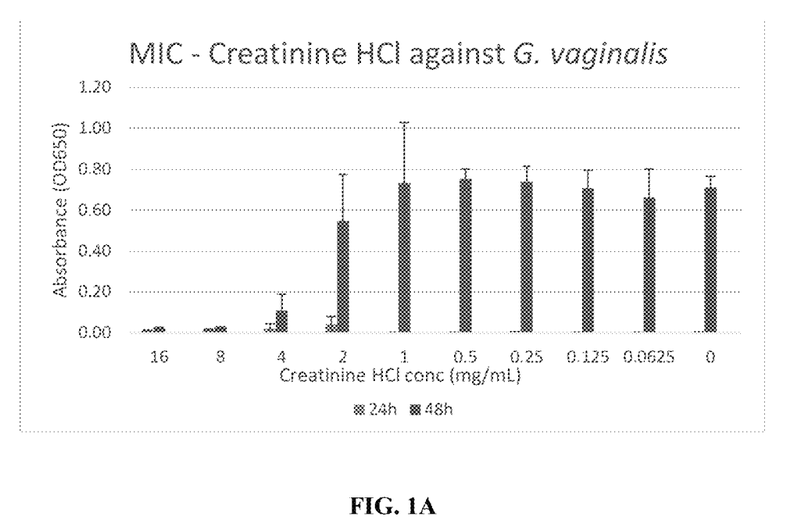
FIG. 1A is a bar graph illustrating the variation in minimum inhibitory concentration (MIC) of creatinine HCl compositions tested for antibacterial activity against *G. vaginalis*.
Figure 1B:
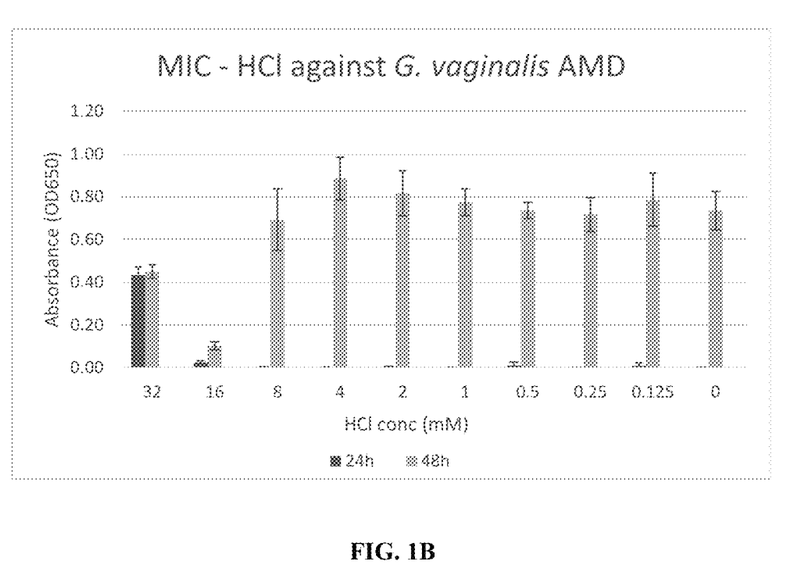
FIG. 1B is a bar graph illustrating the variation in MIC of HCl compositions tested for antibacterial activity against *G. vaginalis*.

FIG. 1A is a bar graph of the results and illustrates the variation in MIC of the creatinine HCl compositions. As shown in FIG. 1A, the composition having 4 mg/mL creatinine hydrochloride showed significant inhibition of growth of G. vaginalis after 48 hours. FIG. 1B is a bar graph illustrating the variation in MIC of pure hydrochloride compositions. As demonstrated in FIG. 1B, the solution of 16 mM hydrochloride, with pH 4.8, inhibited growth of G. vaginalis.

Example 2: Creatinine Hydrochloride Inhibited Growth of M. mulieris

Formulations of creatinine hydrochloride were prepared in different concentrations to evaluate the effect on the inhibition of growth of M. mulieris. Creatinine hydrochloride was used in varying concentrations ranging from 0.0625 mg/mL to 16 mg/mL. The minimum inhibitory concentration (MIC) for each solution was determined against M. mulieris using two-fold dilutions and flat-bottom 96-well plates. For anaerobic bacteria, the MIC is the concentration where no growth, or the most significant reduction in growth is observed after 48-hour incubation (Clinical and Laboratory Standards Institute M11-A6: Methods for Antimicrobial Susceptibility Testing of Anaerobic Bacteria; Approved Standard—$6^{th}$ Edition).

Figure 2A:
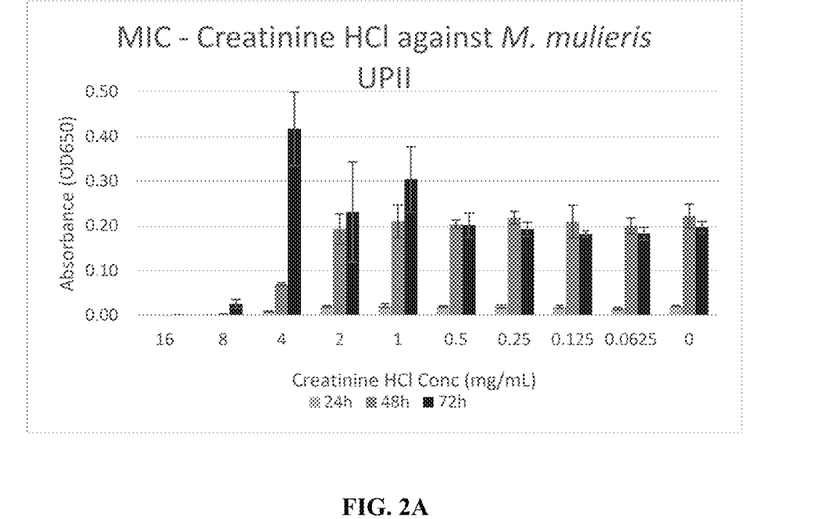
FIG. 2A is a bar graph illustrating the variation in MIC of creatinine HCl compositions tested for antibacterial activity against *M. mulieris*.
Figure 2B:
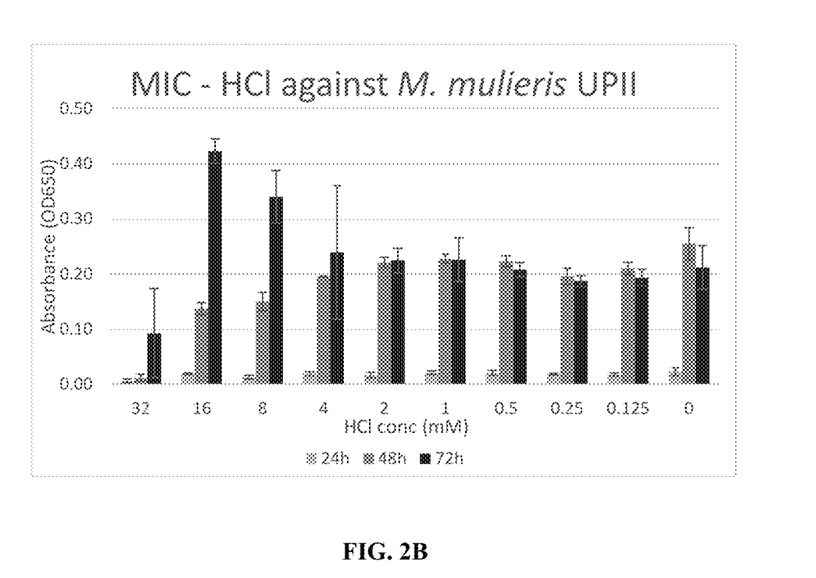
FIG. 2B is a bar graph illustrating the variation in MIC of HCl compositions tested for antibacterial activity against *M. mulieris*.

FIG. 2A is a bar graph of the results and illustrates the variation in MIC of the creatinine HCl compositions. As shown in FIG. 2A, the composition having 4 mg/mL creatinine hydrochloride inhibited growth of M. mulieris after 48 hours. The composition having 8 mg/mL creatinine hydrochloride still inhibited growth of M. mulieris after 72 hours. FIG. 2B is a bar graph illustrating the variation in MIC of pure hydrochloride compositions.

Prophetic Example 3

Subjects presenting with symptoms of BV are identified. A medical assessment as well as culturing is performed for diagnosis and a pH test. The subjects are treated with the following composition:

600 mg of boric acid and 33 µg protonated creatinine.

A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of BV, such as abnormal vaginal discharge, vaginal itching, vaginal odor, and burning during urination.

Prophetic Example 4

Subjects presenting with symptoms of BV are identified. A medical assessment as well as culturing is performed for diagnosis and a pH test. The subjects are treated with the following composition:

600 mg of boric acid and 400 mg protonated creatinine.

A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours after administration of the disclosed composition, each of the subjects experience alleviation of one or more of the symptoms of BV, such as abnormal vaginal discharge, vaginal itching, vaginal odor, and burning during urination.

Prophetic Example 5

Subjects presenting with symptoms of BV are identified. A medical assessment as well as culturing is performed for diagnosis and a pH test. The subjects are treated with the following composition:

600 mg of boric acid and 10 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours after administration of the disclosed composition, each of the subjects experience alleviation of one or more of the symptoms of BV, such as abnormal vaginal discharge, vaginal itching, vaginal odor, and burning during urination.

Prophetic Example 6

Subjects presenting with symptoms of BV were identified. A medical assessment as well as culturing is performed for diagnosis and a pH test. The subjects are treated with the following composition:

300 mg of boric acid and 100 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours after administration of the disclosed composition, each of the subjects experience alleviation of one or more of the symptoms of BV, such as abnormal vaginal discharge, vaginal itching, vaginal odor, and burning during urination.

Prophetic Example 7

Subjects presenting with symptoms of BV are identified. A medical assessment as well as culturing is performed for diagnosis and a pH test. The subjects are treated with the following composition:

300 mg of boric acid and 300 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours after administration of the disclosed composition, each of the subjects experience alleviation of one or more of the symptoms of BV, such as abnormal vaginal discharge, vaginal itching, vaginal odor, and burning during urination.

Prophetic Example 8

Subjects presenting with vaginal odor are identified. The subjects are provided with a spray to apply as needed with the following components: protonated creatinine, boric acid, citric acid, sodium phosphate (dibasic), and water.

A total of 60 subjects participate in the study. All report reduced vaginal odor within about 24 hours after administration of the disclosed spray.

Prophetic Example 9

Subjects presenting with symptoms of BV are identified. A medical assessment as well as culturing is performed for diagnosis and a pH test. The subjects are treated with the following composition:

33 µg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of BV, such as abnormal vaginal discharge, vaginal itching, vaginal odor, and burning during urination.

Prophetic Example 10

Subjects presenting with symptoms of BV are identified. A medical assessment as well as culturing is performed for diagnosis and a pH test. The subjects are treated with the following composition:

400 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours after administration of the disclosed composition, each of the subjects experience alleviation of one or more of the symptoms of BV, such as abnormal vaginal discharge, vaginal itching, vaginal odor, and burning during urination.

Prophetic Example 11

Subjects presenting with symptoms of BV are identified. A medical assessment as well as culturing is performed for diagnosis and a pH test. The subjects are treated with the following composition:
10 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours after administration of the disclosed composition, each of the subjects experience alleviation of one or more of the symptoms of BV, such as abnormal vaginal discharge, vaginal itching, vaginal odor, and burning during urination.

Prophetic Example 12

Subjects presenting with symptoms of BV were identified. A medical assessment as well as culturing is performed for diagnosis and a pH test. The subjects are treated with the following composition:
100 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours after administration of the disclosed composition, each of the subjects experience alleviation of one or more of the symptoms of BV, such as abnormal vaginal discharge, vaginal itching, vaginal odor, and burning during urination.

Prophetic Example 13

Subjects presenting with symptoms of BV are identified. A medical assessment as well as culturing is performed for diagnosis and a pH test. The subjects are treated with the following composition:
300 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are evaluated with a pH test and assessed for symptom expression after the first day of treatment, after the third day of treatment, after the fifth day of treatment, and after the seventh day of treatment.

Within about 24 hours after administration of the disclosed composition, each of the subjects experience alleviation of one or more of the symptoms of BV, such as abnormal vaginal discharge, vaginal itching, vaginal odor, and burning during urination.

Prophetic Example 14

Subjects presenting with symptoms of *chlamydia* are identified. A medical assessment as well as culturing is performed for diagnosis. The subjects are treated with the following composition:
33 µg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of *chlamydia*, such as abnormal vaginal discharge and burning during urination.

Prophetic Example 15

Subjects presenting with symptoms of *chlamydia* are identified. A medical assessment as well as culturing is performed for diagnosis. The subjects are treated with the following composition:
400 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of *chlamydia*, such as abnormal vaginal discharge and burning during urination.

Prophetic Example 16

Subjects presenting with symptoms of *chlamydia* are identified. A medical assessment as well as culturing is performed for diagnosis. The subjects are treated with the following composition:
10 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of *chlamydia*, such as abnormal vaginal discharge and burning during urination.

Prophetic Example 17

Subjects presenting with symptoms of *chlamydia* are identified. A medical assessment as well as culturing is performed for diagnosis. The subjects are treated with the following composition:
100 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of *chlamydia*, such as abnormal vaginal discharge and burning during urination.

Prophetic Example 18

Subjects presenting with symptoms of *chlamydia* are identified. A medical assessment as well as culturing is performed for diagnosis. The subjects are treated with the following composition:
300 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of *chlamydia*, such as abnormal vaginal discharge and burning during urination.

Prophetic Example 19

Subjects presenting with symptoms of gonorrhea are identified. A medical assessment as well as culturing is performed for diagnosis. The subjects are treated with the following composition:
33 µg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of gonorrhea, such as increased vaginal discharge, burning during urination, and vaginal bleeding between periods.

Prophetic Example 20

Subjects presenting with symptoms of gonorrhea are identified. A medical assessment as well as culturing is performed for diagnosis. The subjects are treated with the following composition:
400 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of gonorrhea, such as increased vaginal discharge, burning during urination, and vaginal bleeding between periods.

Prophetic Example 21

Subjects presenting with symptoms of gonorrhea are identified. A medical assessment as well as culturing is performed for diagnosis. The subjects are treated with the following composition:
10 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of gonorrhea, such as increased vaginal discharge, burning during urination, and vaginal bleeding between periods.

Prophetic Example 22

Subjects presenting with symptoms of gonorrhea are identified. A medical assessment as well as culturing is performed for diagnosis. The subjects are treated with the following composition:
100 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of gonorrhea, such as increased vaginal discharge, burning during urination, and vaginal bleeding between periods.

Prophetic Example 23

Subjects presenting with symptoms of gonorrhea are identified. A medical assessment as well as culturing is performed for diagnosis. The subjects are treated with the following composition:
300 mg protonated creatinine.
A total of 90 subjects participate in the study: 30 subjects are treated with the above composition in the form of a suppository capsule, 30 subjects are treated with the above composition in the form of a douche, and 30 subjects are treated with the above composition in the form of an extended release capsule. Each of the subjects are assessed for symptom expression after the first day of treatment, after the third day of treatment, after the fifth day of treatment, and after the seventh day of treatment.

Within about 24 hours to 48 hours after administration of the disclosed composition, each of the subjects experience alleviation of one or more of the symptoms of gonorrhea, such as increased vaginal discharge, burning during urination, and vaginal bleeding between periods.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A method for inhibiting growth of one or more species of bacteria associated with bacterial vaginosis, comprising:
preparing a composition consisting of protonated creatinine, a protonated creatinine salt, or combinations thereof, wherein the protonated creatinine, protonated creatinine salt, or combination thereof is present in the composition in an amount of about 10 mg to about 300 mg; and
subjecting the one or more species of bacteria to the composition.

2. The method of claim 1, wherein the composition is formulated as a vaginal suppository, vaginal capsule, vaginal tablet, coated tampon, or coated condom.

3. The method of claim 1, wherein the composition is formulated as a gel, lotion, spray, ointment, cream, paste, lubricant, or emulsion.

4. The method of claim 1, wherein the composition is formulated for vaginal transmucosal administration.

5. A method for killing one or more species of bacteria associated with bacterial vaginosis, comprising:
preparing a composition consisting of protonated creatinine, a protonated creatinine salt, or combinations thereof, and a weak acid, wherein the protonated creatinine, protonated creatinine salt, or combination thereof is present in the composition in an amount of about 10 mg to about 300 mg and the weak acid is present in the composition in an amount of about 500 mg to about 700 mg; and
subjecting the one or more species of bacteria to the composition.

6. The method of claim 5, wherein the composition is formulated as a vaginal suppository, vaginal capsule, or vaginal tablet.

7. The method of claim 1, wherein the one or more species of bacteria comprise *Gardnerella vaginalis, Mobiluncus mulieris*, or a combination thereof.

8. The method of claim 5, wherein the weak acid is selected from the group consisting of boric acid, lactic acid, ascorbic acid, acetic acid, citric acid, hydrogen sulfide, propionic acid, and carbonic acid.

9. The method of claim 5, wherein the one or more species of bacteria comprise *Gardnerella vaginalis, Mobiluncus mulieris*, or a combination thereof.

10. A method for inhibiting growth of *Gardnerella vaginalis, Mobiluncus mulieris*, or a combination thereof, comprising:
preparing a composition consisting of (i) a protonated creatinine, a protonated creatinine salt, or combinations thereof, (ii) a weak acid, and (iii) a probiotic, prebiotic, or combinations thereof, wherein the protonated creatinine, protonated creatinine salt, or combination thereof is present in the composition in an amount of about 10 mg to about 300 mg and the weak acid is present in the composition in an amount of about 500 mg to about 700 mg; and
subjecting the *Gardnerella vaginalis, Mobiluncus mulieris*, or a combination thereof to the composition.

11. The method of claim 10, wherein the weak acid is selected from the group consisting of boric acid, lactic acid, ascorbic acid, acetic acid, citric acid, hydrogen sulfide, propionic acid, carbonic acid, and combinations thereof.

12. The method of claim 10, wherein the probiotic is of the *Lactobacillus* species.

13. The method of claim 10, wherein the prebiotic is selected from the group consisting of short chain fructo-oligosaccharides, inulin, lactulose, galactooligosaccharide, isomalto-oligosaccharide, soy-oligosaccharide, and xylo-oligosaccharide.

14. The method of claim 5, wherein the weak acid is boric acid.

15. The method of claim 10, wherein the weak acid is boric acid.

\* \* \* \* \*